(12) United States Patent
Pettersson et al.

(10) Patent No.: US 6,429,026 B1
(45) Date of Patent: *Aug. 6, 2002

(54) ONE-STEP ALL-IN-ONE DRY REAGENT IMMUNOASSAY

(75) Inventors: Kim Sverker Immanuel Pettersson, Turku; Timo Nils-Erik Lövgren, Kirjala, both of (FI)

(73) Assignee: Innotrac Diagnostics Oy (FI)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 714 days.

(21) Appl. No.: 08/629,177

(22) Filed: Apr. 8, 1996

(51) Int. Cl.[7] ............................................. G01N 33/543
(52) U.S. Cl. .................... 436/518; 436/287.1; 436/546; 436/800; 436/531; 436/532; 436/809; 435/4; 435/7.92; 435/7.94; 435/810; 435/962; 435/287.2; 435/287.9; 435/969
(58) Field of Search ............................... 436/287.1, 518, 436/546, 800, 531, 532, 809; 435/4, 7.92, 7.94, 810, 962, 287.2, 287.9, 969; 422/57, 58

(56) References Cited

U.S. PATENT DOCUMENTS

| | | | | |
|---|---|---|---|---|
| 4,256,725 A | * | 3/1981 | Rutner et al. .................. | 424/1 |
| 4,434,236 A | * | 2/1984 | Freytag ....................... | 436/512 |
| 4,857,454 A | * | 8/1989 | Freundlich et al. ............ | 435/7 |
| 5,089,423 A | * | 2/1992 | Diamandis et al. ......... | 436/518 |
| 5,378,638 A | * | 1/1995 | Deeg et al. ................. | 436/518 |
| 5,459,045 A | * | 10/1995 | Sato et al. ................. | 435/7.93 |

OTHER PUBLICATIONS

Walter Et Al. 1983, Anal. Chen, 55:873–878.*
Kakabakos Et Al. 1992. Clin.Chem. 38(3):338–342.*
Xu Et Al. 1992. Clin Chem. 38(10) : 2038–2043.*
Rabitzsch Et Al. 1995. Clin. Chem. 41(7):966–978.*
Mair Et Al. 1995. Clin. Chem. 41(9):1266–1272.*
Ohman Et Al. 1993. Br. Heart J., 1996, 63:335–338.*

\* cited by examiner

*Primary Examiner*—Jennifer Graser
(74) *Attorney, Agent, or Firm*—Rothwell, Figg, Ernst & Manbeck, p.c.

(57) ABSTRACT

The invention relates to a novel competitive or non-competitive immunoassay comprising the steps of immobilizing an assay specific component on a solid phase in a reaction well, adding a labelled assay specific component, drying said components, adding the sample containing the marker to be analyzed, allowing the marker to react with the assay specific components, and detecting the signal from the label. Furthermore, the invention relates to a device useful in carrying out the novel assay.

50 Claims, 6 Drawing Sheets

ONE-STEP ALL-IN-ONE DRY REAGENT IMMUNOASSAY

This invention relates to a novel immunoassay in which all the necessary assay specific components are beforehand added to the reaction well and dried before the sample is added. The invention further relates to a device useful in carrying out said assay.

BACKGROUND OF THE INVENTION

The publications and other materials used herein to illuminate the background of the invention, and in particular, cases to provide additional details respecting the practice, are incorporated by reference. Lanthanide chelate labels and time-resolved fluorometry were introduced in the field of immunoassays already more than 10 years ago (Siitari et al. Nature 301, 258–60, 1983). The availability of monoclonal antibodies in combination with the high specific activity of the label enabled non-competitive immunoassays with superior sensitivity and dynamic range to be carried out (Ekins and Dakubu, Pure Appl Chem 57,473–82, 1985, Lövgren and Petterssson in: Van Dyke K and Van Dyke R eds. Luminescece Immunoassays and Molecular Applications. Boca Raton, U.S.A: CRC Press Inc., 233–50,1990). Several different label alternatives with high specific activities have since appeared (Kricka Clin Chem 40,347–57,1994, Price and Newman eds., Principles and Practice of Immunoassays. New York: Stockton Press, 650pp,1991, Dickson et al. Pharmac Ther 66,207–35,1995). Monoclonal antibodies have extensively replaced polyclonal antibodies and a non-competitive assay design is preferred whenever possible. Especially the usefulness of the new non-isotopic labels contributed to the present level of automation of field of immunoassays.

Alternative strategies can be selected to improve the sensitivity and reliability of immunoassays (Kricka Clin Chem 40,347–57,1994, Price and Newman eds., Principles and Practice of Immunoassays. New York: Stockton Press, 650pp,1991, Dickson et al. Pharmac Ther 66,207–35,1995, Ekins and Chu Clin Chem 37,1955–67,1991). As the potential sensitivity of a non-competitive immunoassay can be realized only by using labels with a high specific activity together with high-affinity antibodies (Ekins and Dakubu, Pure Appl Chem 57,473–82, 1985, Ekins and Chu Clin Chem 37,1955–67,1991) considerable effort is spent on the search for more sensitive detection technologies. Besides factors such as detector noice, interference in the sample causing a nonspecific signal, and nonspecific binding of the label reagent reduce the overall assay sensitivity (Ekins and Dakubu, Pure Appl Chem 57,473–82, 1985, Lövgren and Petterssson in: Van Dyke K and Van Dyke R eds. Luminescece Immunoassays and Molecular Applications. Boca Raton, U.S.A: CRC Press Inc., 233–50,1990). Other reasons to design novel immunoassay strategies are to improve the reliability by high quality key reagents and to simplify the assay by eliminating unnecessary steps to obtain more direct procedures.

The time-resolved fluorometry and lanthinide chelate label based immunoassay technology was originally based upon the dissociation enhanced lanthanide fluoroimmunoassay (DELFIA) concept (Hemmilä et al. Anal Biochem 137,335–43,1984). The high specific activity of the label that could be covalently bound to monoclonal antibodies without any effects on the affinity and specificity (Lövgren and Petterssson in: Van Dyke K and Van Dyke R eds. Luminescece Immunoassays and Molecular Applications. Boca Raton, U.S.A: CRC Press Inc., 233–50,1990) proved to be very useful in the design of several non-competitive assays with improved sensitivity (Pettersson et al. Clin Chem 29,60–4,1983, Nantö et al. Isr J Clin Biochem Lab Sci 4,36,1985, Suonpää et al. Clin Chem Acta 145,341–8,1985, Hemmiläin:Winefordner ed. Chemical Analysis, Vol 117. Toronto: Wiley & Sons, 343pp,1991, Xu et al. Clin Chem 38,2038–43,1992). Furthermore competitive assays (Bertoft et al. FEBS Lett 173,313–6,1984, Eskola et al. Clin Chem 31,1731–4,1985, Nantö et al. Isr J Clin Biochem Lab Sci 4,52,1985, Lövgren Steroid Biochem 27,47–51,1987) with good performance chracteristics were carried out although the label does not essentially contribute to the sensitivity in this assay design (Ekins and Dakubu, Pure Appl Chem 57,473–82, 1985, Ekins and Chu Clin Chem 37,1955–67, 1991).

The immunoassays carried out in a routine laboratory have been subject to extensive automation. The analyzers should operate in a fast random and continuous access mode. The throughput capacity should be similar to that of general chemistry analyzers and a large on-board supply of reagents should reduce the operators hands-on time. The automation requirements have turned out to be difficult for most label technologies and the performance characteristics of the analytes in the panels have suffered because of compromises that had to be made. In the present invention we describe a relatively fast immunoassasy technology suitable for automation in which all assays are performed in one-step procedures in microtitration wells containing all the assay specific reagents necessary for one test in dry form. An intrinsically fluorescent stable lanthanide chelate with a high specific activity is used as the label. The performance of the model assays has been tested in quantitative measurements biochemical cardiac markers in whole blood for the early detection of acute myocardial infarction (AMI).

Early confirmation or exclusion of AMI is essential for the correct treatment decision (Rozenman Y et al., Annu Rev Med 1994;45:31–44 and L Kristein Newby et al., Clin Chem 1995;41:1263–1265). Because half of all AMI patients have nondiagnostic ECGs at the time of admission, biochemical markers are often required to confirm diagnosis. Unfortunately laboratory results on biochemical markers are usually not available until several hours after the first diagnosis and eventual admission of the patient. More than 50% of the deaths occur within the first 2 hours after the onset of symptoms. In addition, the availability of thrombolytic therapy and the clear benefit of early intervention emphasize the need for rapid diagnosis. Optimally results on biochemical markers should be available simultaneously with the ECG data. Still the sensitivity of the creatine kinase MB isoenzyme (CK-MB) activity measurement, the most accepted protein marker, is too low to accurately rule in or rule out myocardial injury during these early hours.

Myoglobin (Mb) is a 17 800 kDa heme protein present in cardiac and skeletal muscle. Due to its low molecular mass, Mb is realesed early (2–4 h) from the injured cardiac muscle, and transferred to the serum. The fast rise of Mb in patients with AMI makes it an ideal marker for early confirmation or exclusion of AMI and for monitoring cardiac reperfusion (Ohman EM et al., Br Heart J 1990;63:335–338). However, the lack of rapid availability of quantitative results has limited its clinical application.

The optimal advantage of Mb and other biochemical cardiac marker would be gained with quantitative assays with a turn-around time short enough to offer results simultaneously with the ECG to be analyzed by the clinician. One of the rate-limiting steps in the assays of most early biochemical markers includes manual separation of plasma or serum from whole blood. The possibility to use a direct assay on whole blood samples would shorten the total time from the blood collection to the interpretation of the result notably. Our aim was therefore to optimize a rapid time-resolved immunofluorometric assay suitable for simple automatic processing of whole blood samples to yield highly reproducible quantitative results on Mb and other biochemical cardiac markers in order to make results available for early diagnosis of AMI.

SUMMARY OF THE INVENTION

An immunoassay has been invented in which all assay specific components are beforehand added to the reaction well and dried before the well is used in immunoassays to quantitatively measure analytes in e.g. serum, plasma or whole blood samples. According to the invention biochemical markers, especially biochemical cardiac markers, can be measured directly from whole blood samples for the early detection or ruling out of acute myocardial infarction by using a time-resolved fluoroimmunoassay and intrinsically fluorescent lanthanide chelates. A whole blood sample is added in a suitable assay solution or buffer into small reaction wells or ordinary microtitration wells containing all assay specific components in a dry form. The immunoassay can be either competitive or non-competitive and more than one cardiac marker can be measured in one reaction well or microtitration well when different lanthanide chelate labels (europium, terbium, samarium and dysprosium) are used simultaneously for the assay of individual biochemical cardiac markers. After the immunoreaction has been completed (reached equilibrium) or interrupted (kinetic measurement) the reaction wells or microtitration wells are washed with the assay solution and the time-resolved fluorescence from the intrinsically fluorescent lanthanide chelate label is measured. The fluorescence is either measured directly from the surface of the reaction well or microtitration well or after the intrinsically fluorescent lanthanide chelate has been brought into a solution. The time-resolved fluorescence signal level is a quantitative measure of the determined biochemical cardiac marker. Typically measured cardiac markers are myoglobin, creatine kinase MB isoenzyme (CK-MB), troponin I and troponin T.

BRIEF DESCRIPTION OF THE DRAWINGS

FIG. 1A) and competitive (FIG. 1B) immunoassay.

DETAILED DESCRIPTION OF THE INVENTION

Non-competitive and competitive immunoassays are routinely used in clinical laboratories to measure physiologically important protein markers in serum and plasma samples. In the early diagnosis of AMI a rapid, easy-to-perform, one-step immunoassay yielding quantitative results with whole blood 'samples would be particularly useful for detection of biochemical cardiac markers. Particularly Mb but also CK-MB, creatine kinase isoform ratio s, troponin I and troponin T are considered suitable for both early detection of AMI and for monitoring of reperfusion because it is elevated in the blood soon after the onset of symptoms Johannes Mair et al., Clin Chem 1995;41:1266–1272). The recently introduced assay for glycogen phosphorylase isoenzyme BB represents another rapid and sensitive marker for myocardial injury (Georg Rabitzsch et al., Clin Chem 1995;41:966–978). Rapid immunofluorometric assays of these biochemical cardiac markers could be used to provide quantitative, highly reproducible results with whole blood samples.

The use of time-resolved fluorometry and a monoclonal antibody labeled with an intrinsically fluorescent lanthanide chelate with high specific activity enable the use of a small sample and assay volume resulting in fast kinetics, good sensitivity and a wide dynamic measuring range. The achieved low limits of detection with whole blood assays are adequate and the standard curves are linear over the whole measurement range and yet the high dose hook effect does not interfere with the assay. Moreover, the possible use of a small sample volumes minimizes the potential interference with whole blood samples.

The possibility to use whole blood samples eliminates the time required for the manual separation of plasma or serum. The predilution of the sample followed by one-step assay is easily automated to give quantitative results in less than 20 min. Essentially identical results can be obtained using only a 5 min incubation time although equilibrium is not reached in the assay. Furthermore, the possible imprecion in the manual procedure due to the inaccurate transfer of the small sample and reagent volumes used, will be eliminated by the automation of the assay system. Thus the quantitative results of biochemical cardiac markers can be made available within the same time frame as the ECG data. It is feasable that a whole panel of biochemical markers for the diagnosis of AMI can be quantitatively measured from whole blood samples. Because of the biochemical serum markers, different release patterns rapid results on e.g. myoglobin, CK-MB and troponin I will help in the diagnosis of patients arriving different times after the onset of symptoms.

Figure 1A:
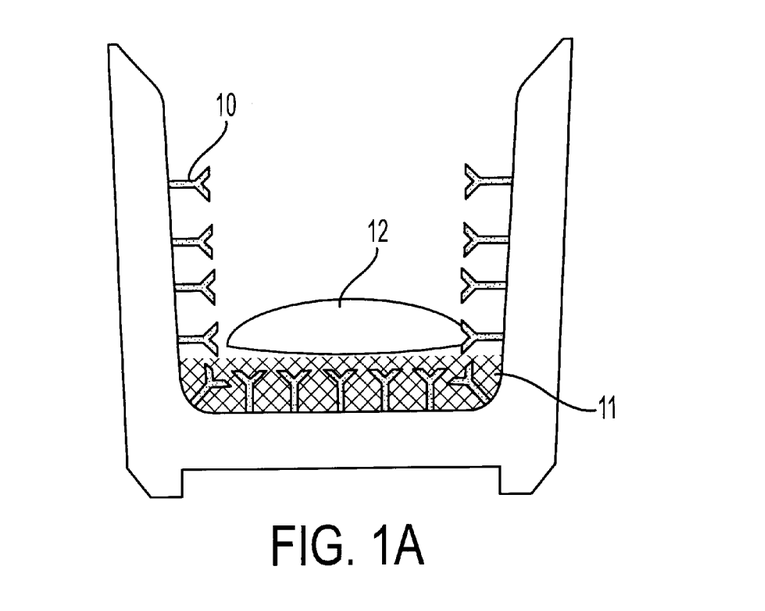
FIGS. 1A and 1B show the principal design of the one-step all-in-one dry reagent non-competitive (sandwich.
Figure 1B:
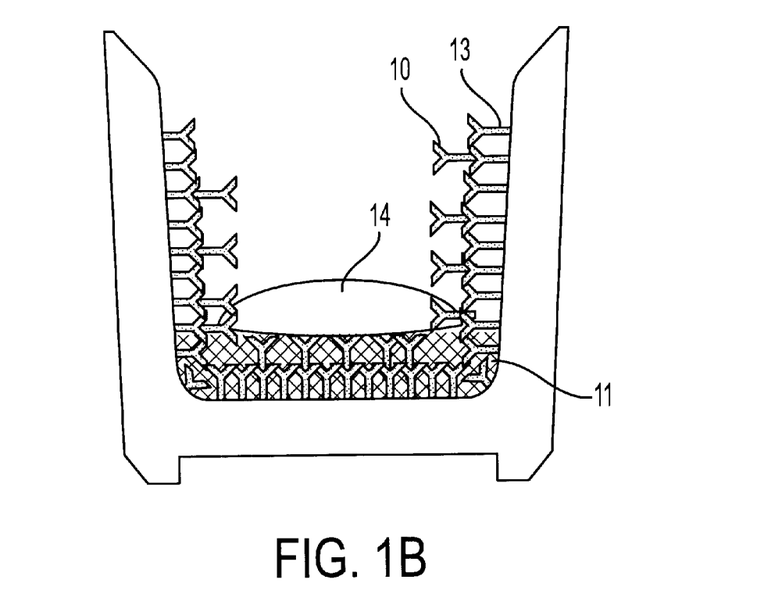

The immunoassay design allows both non-competitive and competitive assays to be carried out (FIGS. 1A and 1B). In the non-competitive assay (FIG. 1A) the analyte specific catching antibody 10 is immobilized either directly onto the surface of the well, or the biotinylated catching antibody is immobilized onto the surface of a streptavidin coated well. Also other indirect coating procedures based on secondary immobilizing reagents can be used to immobilize the analyte specific catching antibody. An insulating layer 11 containing carbohydrate and/or protein and optional protein addition is dried on top of the catching antibody in the bottom of the well. Finally the labeled antibody 12 is added in a small volume on top of the insulating layer and dried. The competitive assay (FIG. 1B) contains a secondary antibody 13 and the analyte specific antibody 10 immobilized onto the surface of the well. An insulating layer 11 is used containing optional protein additives as well as blocking agents and the labeled competing analyte 14 is dried in a small volume on top of the insulating layer. Alternatively the insulating layer is omitted and the labeled competing analyte is added in a small volume directly on the top of the specific antibody and dried. To start the immunoassay only the sample (or standard) and a common assay buffer needs to be added.

The effect of the insulating layer composition in the dry reagent well on the performance of the immunoassay was investigated. The influence of several additives such as carbohydrates, proteins and blocker components were tested using various amounts, volumes and drying temperatures. In a non-competitive immunoassay the labeled component has to be dispensed on top of the insulating layer in a small volume and dried immediately. In a competitive immunoassay the labeled component can alternatively be added directly on top of the specific antibody. The performance of the all-in-one dry reagent concept was always compared with an immunoassay with the corresponding components in solution. An insulating layer made out of protein and carbohydrate provides the lowest background and highest signal to noice ratio when compared with the other alternatives. With a proper insulating layer an assay performance is achiewed that is at least equivalent to the one obtained with all assay components in solution.

Although the immunoassay according to this concept is carried out in a conventional microtiter well format it has been proven that performance characteristics in accordance to the present state-of-art are achieved. The detection and label technology, time-resolved fluorometry and the fluorescent europium chelate (Soini and Lovgren CRC Crit Rev Anal Chem 18,105–154,1987, Dickson et al. Pharmac Ther 66,207–35,1995), due to the high sensitivity, the inert, lenient and stable label, and the wide dynamic range make this possible. Consequently, relatively small sample volumes can be used while still reading low limits of detection for the analytes. The kinetics or reaction rate of the assays can be increased by reducing the total assay volume and by incubation at higher temperatures. The reaction rate of the non-competitive assays is further improved by adding an increased amount of the labeled antibody which also decreases the high dose hook effect. All the model assays included in the evaluation of the one-step all-in-one dry reagent concept reached eguilibrium in less than 15 minutes when optimized in reagard to the factors mentioned. Obviously much faster assays can be performed according to the same concept if the requirement for equilibrium is abandoned.

According to the presented concept no two-step assays are accounted for because then a reagent addition step has to be included. Ordinary competitive assays are usually carried out in a one-step procedure. In a non-competitive assay this can occaisionally be considered as a limitation. The high capacity of the solid phase as well as the label technology which allows the use of increased amounts of the labeled antibody compensates this limitation. The signal caused by a high dose hook effect will never decline below the signal obtained for the highest standard used for the analyte in question.

The intrinsically fluorescent lanthanide, e.g. europium, chelate is bound to the labeled component in the immunoassay both during incubation and measurement phase. In the dissociation enhanced lanthanide fluoroimmunoassay (DELFIA) the europium ion is dissociated from the chelate used for labeling into a solution where a new fluorescent complex is formed (Hemmila et al. Anal Biochem 137, 335–43,1984). The new intrinsically fluorescent lanthanide chelates have a specific activity equal to that obtained in the DELFIA procedure. The release of the fluorescent labeled component from the solid phase into solution for the time-resolved measurement is fast (Mitrunen et al. Clin Chem 41,1115–20,1995, Diamandis et al. Clin Biochem 25,255–61,1992). The risk for exeternal contamination is minimized as the lanthanide ion is never released from the chelate before the measurement. Dual-label assays using fluorescent europium and terbium chelates are possible (Mitrunen et al. Clin Chem 41,1115–20,1995) and alternatively the fluorescent signal can be measured directly from the solid-phase surface which excludes all release steps.

The detection limit of one of the intrinsically fluorescent europium chelates 4-(2-(4-isothiocyanatophenyl)ethynyl)-2, 6,-bis((N,N-bis(carboxymethyl)-amino)methyl)pyridine was measured. Several similar intrinsically fluorescent lanthanide chelates have been synthesized (Mukkala et al. Helv Chim Acta 75,1621–32,1992). In contrast to the DELFIA enhancement principle for the measurement of europium the lanthanide is all the time bound to the original chelate and the excitation energy is efficiently absorbed by the energy mediating moiety of the molecule. The detection limit (background +2SD) for the fluorescent europium chelate was estimated to $5 \times 10^{-14}$ mol/L which corresponds to the detection limit of europium in the DELFIA enhancement solution (Hemmilä et al. Anal Biochem 137,335–43,1984).

The inert and stable intrinsically fluorescent lanthanide chelate label makes the one-step all-in-one dry reagent immunoassay feasible. The possible non-specific binding of the labeled component is prevented by the use of an insulating layer in the all-in-one dry reagent well. In case the insulating layer is omitted the non-specific binding increases especially in the high excess reagent, non-competitive assays during storage of the well. Optimally the one-step all-in-one dry reagent non-competitive immunoassay with both protein and carbohydrate added in the insulating layer performed better than the corresponding assay employing reagents in liquid form. Some of the additives and obviously the blockers were analyte specific. The addition of the labeled component on top of insulating layer is also crucial. Particularly in the non-competitive assays the labeled antibody has to be added in a small volume that is rapidly dried in order to keep the non-specific binding insignificant. In a competitive assay the use of an insulating layer is not essential as long as the assay is carried out to equilibrium. Once the analyte specific optimazation of the one-step all-in-one dry reagent well has been carried out their use is extremely simple as only the sample and a common assay buffer or solution are required when the immunoassay is performed.

The following examples are offered by way of illustration and not limitation.

EXPERIMENTALS

Example 1

Labeling of Monoclonal Antibodies

The Mab used in detection was labeled with a fluorescent chelate of 4-(2-(4-isothiocyanato-phenyl)ethynyl)-2,6,-bis ((N,N-bis(carboxymethyl)-amino)methyl)-pyridine of europium (Eu). Labeling was performed overnight at 4° C. with a 100-fold molar excess of the Eu chelate in a buffer containing 50 mmol/L $NaHCO_3$ (pH 9.8). A high protein concentration (up to 3.3 mg/mL) and thus a lower excess of chelate was used in order to minimize the total volume of the labeling reaction. A Superdex 200 HR 10/30 column (Pharmacia LKB, Uppsala, Sweden) with a high precision pump P-500 (Pharmacia LKB) was used to separate the labeled antibody from excess of chelate. The elution buffer used contained per liter, 50 mmol of Tris-HCl, 9 g of NaCl, and 0.5 g of NaN$_3$, pH 7.75 (TSA-buffer). Fractions containing the labeled protein were pooled and the labeling degree of the antibody was determined. A known amount of the labeled mAb was incubated in an anti-mouse IgG coated well (Wallac oy), the wells were washed 6 times, and DELFIA Enhancement solution (Wallac Oy) was added in order to measure the fluorescence of the bound europium against a Eu standard. The mAb contained 7–8.3 Eu per IgG. A final concentration of 1 g/L of diethylenetriaminepentaacetic acid (DTPA) purified BSA was added and the pool was filtered through 0.2 µm filter to remove aggregates. The labeled mAb was stored at 4° C.

Example 2

Biotinylation of Monoclonal Antibodies

The mAb used in the capture was reacted with a 100-fold molar excess of isothiocyanate derivative of biotin (BITC, Wallac Oy) dissolved in N,N-dimethylformamide (10 mmol) in a buffer containing 50 mmol/L of NaHCO$_3$ (pH 9.8) and incubated for 2–4 hours at room temperature. The free biotin was separated by gel filtration with a NAP-10 column, and subsequently with a PD-10 column (Pharmacia LKB) using TSA-buffer for elution. Finally 1 g/L DTPA-treated BSA was added. The biotinylated mAb was stored at 4° C.

Example 3

Coating Directly with Monoclonal Antibodies

The capture mAb immobilized onto microtitration strips through physical adsorption. The wells were coated with 1 µg of the mAb in 100 µL of buffer containing 0.2 mol/L NaH$_2$PO$_4$ buffer overnight at 35° C. Coated wells were washed twice with Delfia Wash solution by using Delfia platewash, and then saturated for 3 h at room temperature with 300 µl of a solution containing, per liter, 1 g of BSA, 60 g of trehalose, 1 g of Germall II, and 50 mmol of NaH2PO4. After saturation, the wells were aspirated and dried for 2 h at 25° C.

Example 4

Coating with Streptavidin and Immobilization of the Capture mAb

UV-absorbed low-fluorescence Maxisorb strips (Nunc, Roskilde, Denmark) were directly coated overnight at 35° C. with 1 µg/well of streptavidin (Porton Products, United Kingdom) in 0.1 mol/L of citrate-phosphate buffer (pH 5.0) containing per liter 9 g of NaCl. The plates were washed twice with DELFIA Wash solution (Wallac Oy) containing, per liter, 9 g NaCl, 0.1 g Germall II, 0.05 g Tween 20, and 5 mmol Tris-HCl (pH 7.75) supplemented with 0.05% Tween® 20 using DELFIA Platewash (Wallac Oy). Saturation overnight at room temperature was carried out with a buffer containing per liter, 50 mmol Tris-HCl (pH 7.0), 60 g of sorbitol and 2 g of DTPA-treated BSA. Finally the plates were aspirated and air dried.

The capture mAb was immobilized onto streptavidin coated plates by incubating 200 ng of biotinylated mAb in 50 µL of DELFIA Assay buffer (Wallac Oy), containing per liter, 50 mmol of Tris-HCl (pH 7.75), 9 g of NaCl, 5 g of BSA, 0.5 g of bovine-γ-globulin, 0.1 g of Tween 40, 20 µmol of diethylenetriaminepenta-acetic acid (DTPA), 0.5 g NaN$_3$, and 20 mg of cherry red. The strips were incubated 30 min at room temperature with shaking and washed two times and air dried.

Example 5

Preparation of All-in-one Dry Reagent Microtitration Wells

The insulating carbohydrate layer was prepared onto the indirectly or directly immobilized specific catching monoclonal antibody by adding to the coated well 10 µl of a solution containing, per liter, 5 g BSA or casein, 100 g sorbitol, 9 g of NaCl, 0.5 g NaN$_3$3, 0.2 g Tween 20, 1.2 g bovine gammaglobulin, and 50 mmol Tris-HCl, pH 7.7. The solution in the well was dried overnight at 35° C. Assay specific components and blockers as e.g. native mouse IgG, HBR-2 and MAK-33 can be added to this layer. The labeled mAb (300 ng) was dispensed on top of the insulating layer in 1 µL of a solution containing, per liter, 1 g of diethylenetriaminepentaactic acid (DTPA)-treated BSA, 50 g trehalose, 9 g NaCl, 0.05 g cherry red, 0.5 g NaN$_3$, and 50 mmol Tris-HCl, pH 7.75. The dispensed solution was dried immediately by blowing air to the well. The all-in-one dry reagent wells were stored at +4° C. in a sealed package with desiccant.

In a competitive immunoassay the Eu chelate labeled analyte is either added onto the insulating layer or directly on to the analyte specific coated well in a small volume (1 µL) of the solution containing, per liter, 1 g of diethylenetriaminepentaactic acid (DTPA)-treated BSA, 50 g trehalose, 9 g NaCl, 0.05 g cherry red, 0.5 g NaN$_3$, and 50 mmol Tris-HCl$_1$, pH 7.75. The dispensed solution was dried immediately by blowing air to the well. The all-in-one dry reagent wells were stored at +4° C. in a sealed package with desiccant.

Example 6

Immunoassay Procedures

The immunoassays were performed according to the following procedure. Standards and whole blood, plasma, or serum samples were diluted 1:5 in assay buffer. Aliquots of 10 µL of diluted samples in 20 µL of assay buffer were added into the one-step all-on-one dry reagent wells. The well was shaken for 15 minutes at 36° C. using shake speed of 900 rpm with iEMS Incubator/Shaker (Labsystem Oy, Helsinki, Finland) and the excess label was removed by washing the wells six times. The signal of the fluorescent Eu chelate was measured after adding 200 µL of LANFIA solution (Mitrunen et al. Clin Chem 41,1115–20,1995), containing, 25 per liter, 50 mmol of glycine-NaOH, 1.75 mol of NaSCN, 2 mmol of Na$_2$CO$_3$, 50 mL of glycerol, 5 mg of Tween 40, 4.5 µmol of DTPA, and 200 mL of 1-propanol, pH 10.0. The well was shaken for 3 min and measured with DELFIA plate fluorometer, model 1234 (Wallac Oy). Alternatively the time-resolved fluorescence signal was read directly from the surface of the well after the washing step had been completed.

RESULTS

Kinetics

Figure 2:
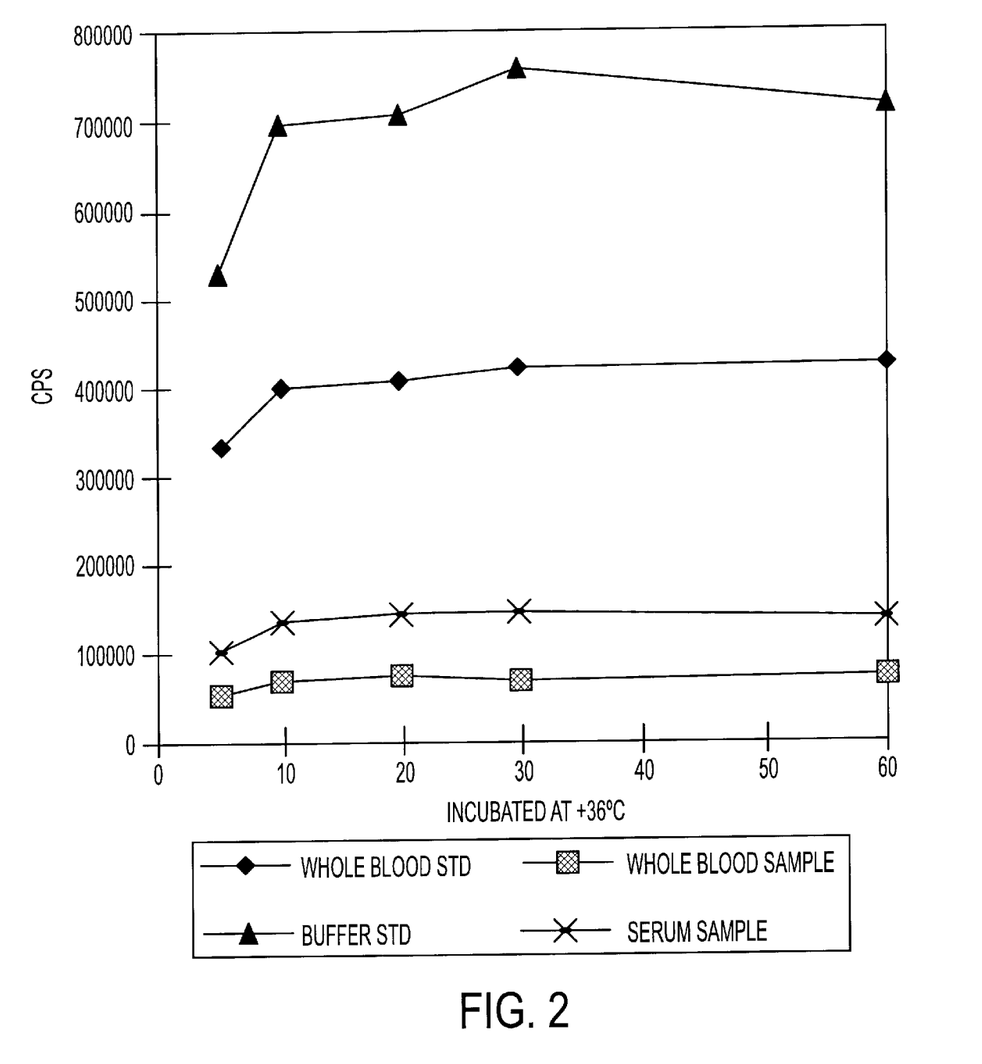
FIG. 2 shows the signal for whole blood standard (filled squares), buffer standard (filled triangles), whole blood sample (dotted squares) and serum sample (X) versus time for incubation at +36° C., determined according to the invention.

Factors affecting the reaction rate of the one-step non-competitive assay were optimized viz. temperature, component concentartion, assay volume and quality of antibodies. The performance of the optimized assay kinetics was confirmed with different standard and sample materials by incubating the microtitration wells containing serum-and whole blood samples, and buffer and whole blood standards for 5, 10, 20, 30 and 60 min at +36° C. with continuous shaking (FIG. 2). Equilibrium was reached in 15 min with all samples.

Range and Linearity

Figure 3:
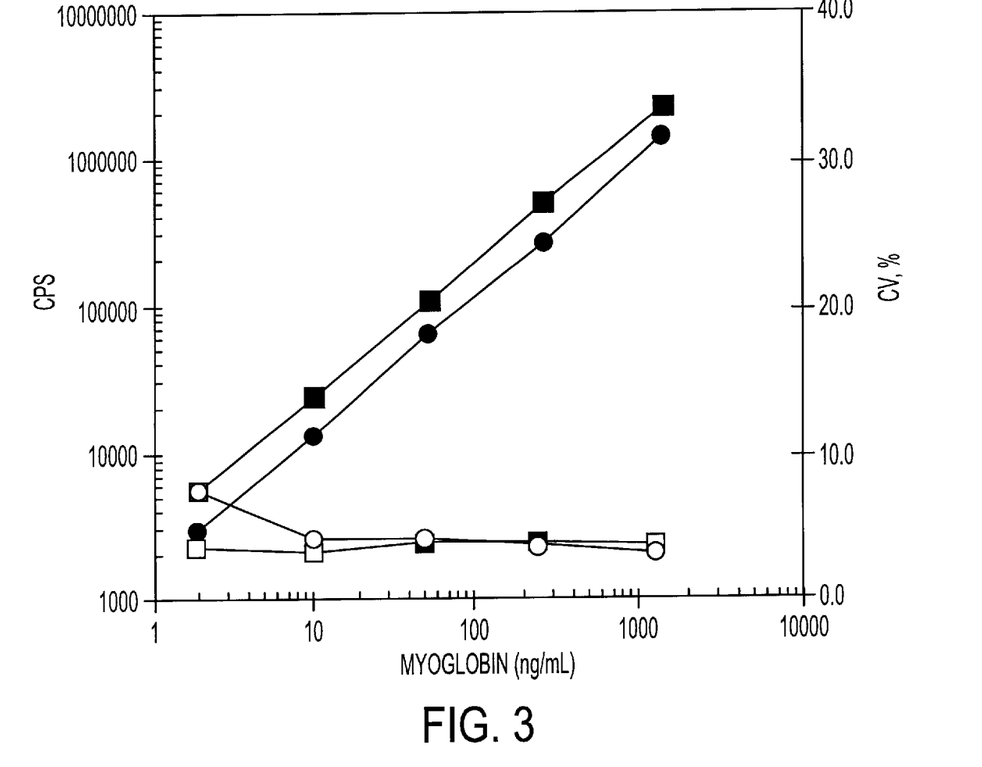
FIG. 3 shows the signal versus myoglobin concentration for buffer standard (filled squares) and whole blood standard (filled circles). The figure further shows CV in % for buffer standard (open squares) and whole blood standard (open circles), determined according to the invention.

The calibration curves for both buffer and whole blood standards were linear over the range from 2 to 1250 µg/L. Within-assay precision (n=12) with buffer standards was 3.2–4.0% and 3.3–7.3% with whole blood standards (FIG. 3). The lowest detectable amount of Mb was 0.1 µg/L for the serum assay and 0.6 µg/L for the whole blood assay when estimated as the dose equivalent to the signal of the mean of 12 replicates of zero standard plus 3 SD.

Precision

The within-assay CVs with both serum and spiked whole blood samples were all below 4% and the between-run CVs were below 5% and 6% respectively (Table 1).

Linearity

Linearity in the measuring range was confirmed by diluting 3 serum samples containing 24.2 µg/L, 43 µg/L and 1103.1 µg/L of Mb 1–32-fold with standard diluent and plotting observed (y) vs. expected (x) myoglobin concentrations. All dilutions were made from the original samples. The 3 diluted serum samples showed a good of linear correlation; y=0.94x−0.13 (r=1.0), y=1.02x−0.38 (r=0.99) and y=0.91x+12.9 (r=0.99), respectively.

Interference Studies

Cross-reaction with hemoglobin was examined by adding increasing amounts of hemolysate (hemoglobin 0–75 g/L) to Mb-depleted serum. Addition of up to 75 g of hemoglobin per liter did not cause any increased assay response.

Recovery

The assay showed good recoveries with both serum and whole blood samples. The average analytical recovery with whole blood (n=5) and serum (n=4) samples was 96% and 100%, respectively (Tables 2 and 3).

Comparison Study

Figure 4:
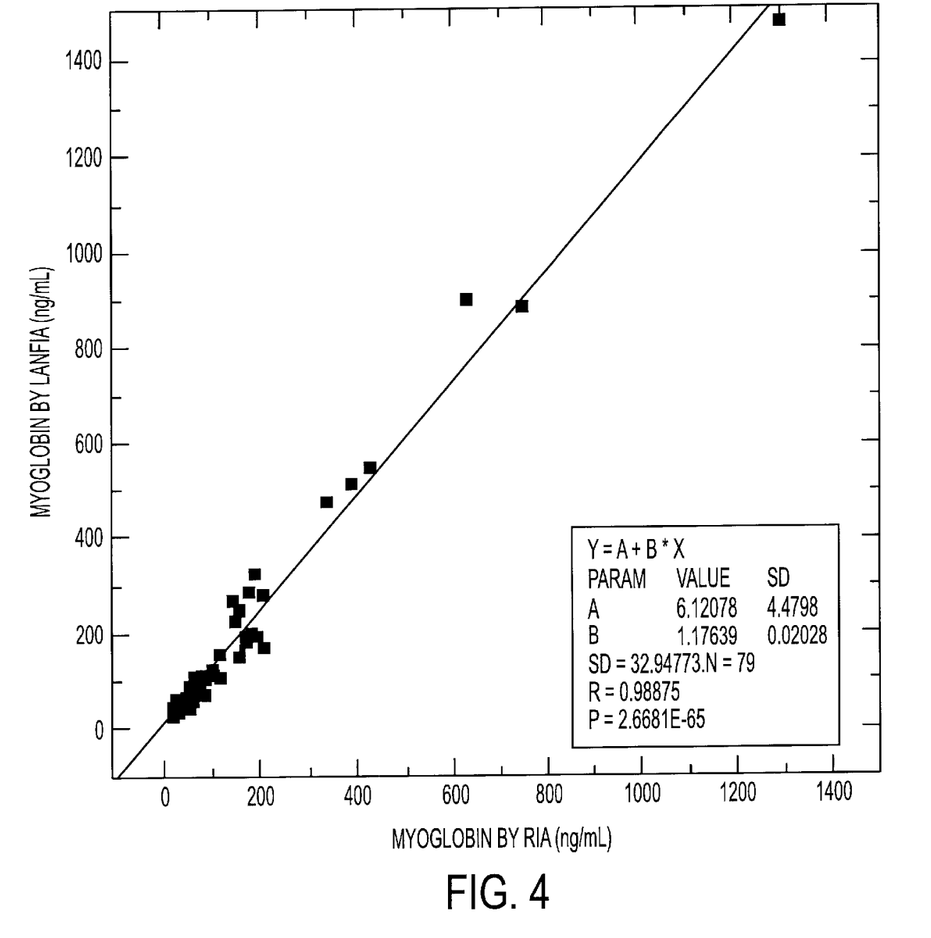
FIG. 4 shows the correlation between myoglobin according to the invention using LANFIA (fluorescent lanthanide chelate in solution) and myoglobin by conventional RIA.

The results obtained by the non-competitive immunofluorometric LANFIA assay using serum samples were compared with those obtained by the DELFIA assay reported by Vuori et al. (Clin. Chem. 37/12, 2087–2092 (1991)) (n=9). The two assays gave results with high degree of correlation: y=0.68x+7.31 (r=0.995). A close correlation was also found between the serum sample results obtained by LANFIA and a commercial RIA kit purchased from Biomerica (Newport Beach, Calif.) (n=79); y=1.25x−0.74, r=0.982 (FIG. 4). The results below the lower limit of detection (20 ng/mL) of the RIA kit were eliminated from the regression analysis.

Correlation Between Whole Blood and Plasma Samples

Figure 5:
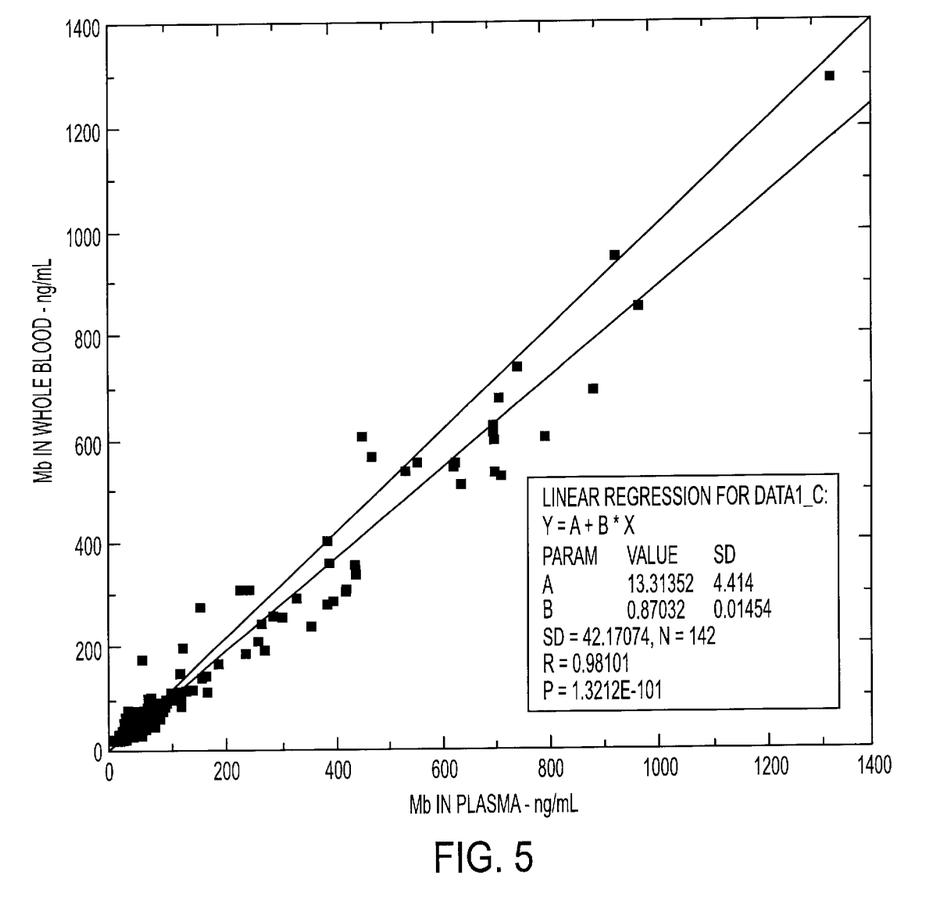
FIG. 5 shows the correlation between myoglobin from whole blood and myoglobin from plasma determined according to the invention.

FIG. 5 shows a comparison of the Mb results obtained with the developed assay using the same samples of either whole blood or plasma, respectively (y=0.87x+13.3, r=0.981).

Patient Results for Myoglobin

Figure 6:
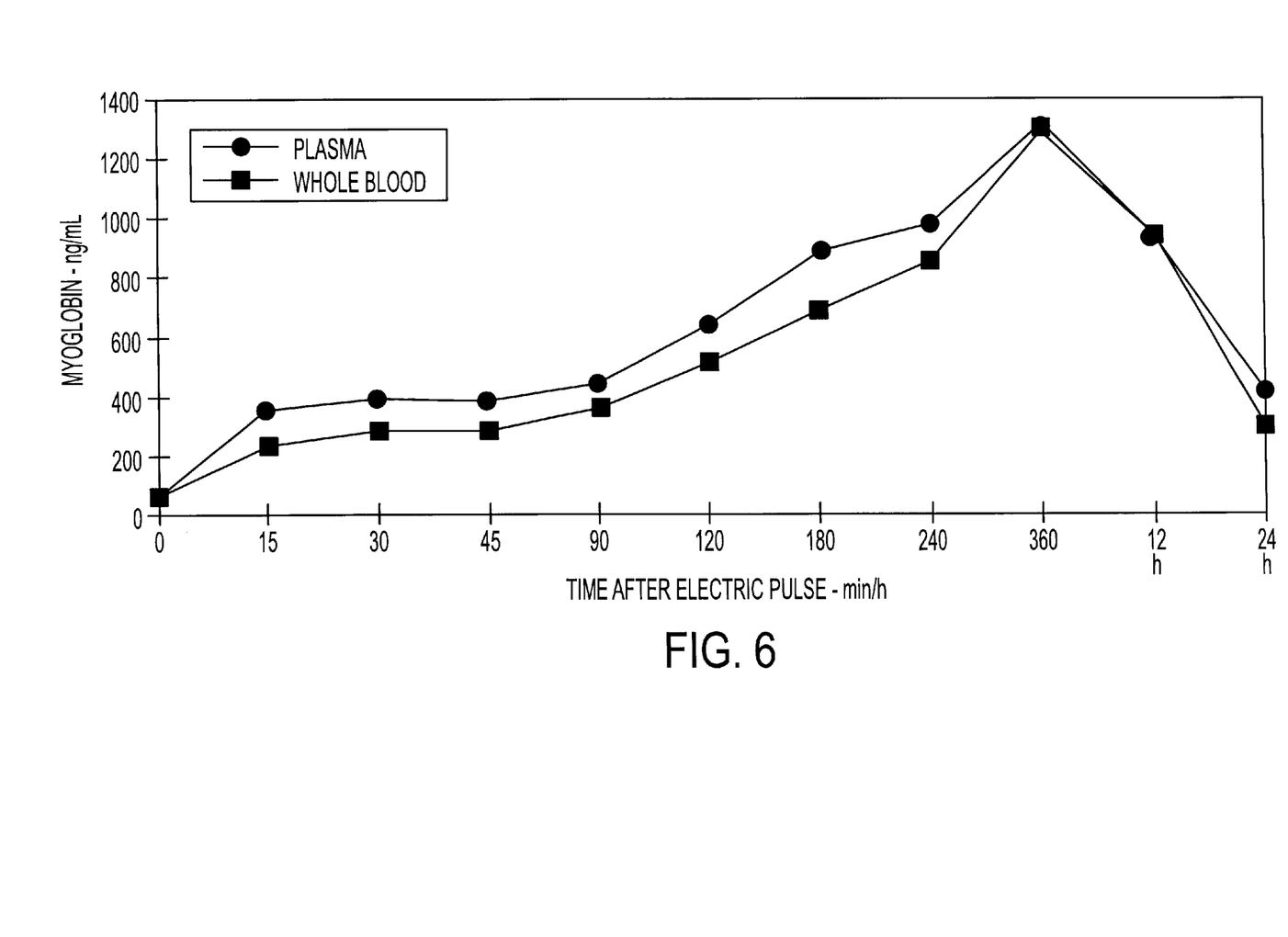
FIG. 6 shows cardioversion patient myoglobin concentration from plasma (filled circles) and whole blood (filled squares) versus time after electric pulse, determined according to the invention.

Whole blood and plasma samples were also taken from cardioversion patients at different times after the electric pulse treatment. A typical result for the Mb release from one cardioversion patient is shown in FIG. 6.

CK-MB Measurements in Whole Blood Samples

Serum and whole blood samples from the same patient were measured according to the invention for their CK-MB concentration. The results are presented in Table 4.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

TABLE 1

Within (n = 12) and between (n = 10) precision with serum and whole blood control samples

| | Serum samples | | | Whole blood samples | | |
|---|---|---|---|---|---|---|
| | mean ng/ml | SD | CV % | mean ng/ml | SD | CV % |
| Control A | | | | | | |
| Within assay | 32.4 | 1.3 | 3.9 | 42.6 | 2 | 2.3 |
| Between assay | 33.4 | 1.4 | 4.3 | 40.5 | 1.6 | 3.9 |
| Control B | | | | | | |
| Within assay | 154.2 | 3.4 | 2.2 | 143.2 | 3.4 | 2.4 |
| Between assay | 158.9 | 7.5 | 4.7 | 143.4 | 8.1 | 5.6 |
| Control C | | | | | | |
| Within assay | 811 | 14.7 | 1.8 | 457.2 | 9.4 | 2.1 |
| Between assay | 857 | 30.5 | 3.6 | 465.3 | 27.5 | 6 |

TABLE 2

Recovery of myoglobin from plasma samples

| endogenous ng/mL | added ng/mL | measured ng/mL | recovery % |
|---|---|---|---|
| 47 | 92 | 134 | 96 |
| 47 | 184 | 232 | 100 |
| 22 | 367 | 414 | 106 |
| 22 | 734 | 738 | 98 |

TABLE 3

Recovery of myoglobin from whole blood samples measured against buffer standards

| endogenous ng/mL | added ng/mL | measured ng/mL | recovery % |
|---|---|---|---|
| 37 | 63 | 96 | 95 |
| 26 | 127 | 145 | 95 |
| 24 | 190 | 209 | 97 |
| 11 | 13 | 24 | 100 |
| 25 | 317 | 319 | 93 |

TABLE 4

CK-MB concentration in serum and in whole blood

| Sample | Serum (ng/mL) | Whole blood (ng/mL) |
|--------|---------------|---------------------|
| 1 | 114.7 | 156.8 |
| 2 | 26.6 | 28.0 |
| 3 | 219.7 | 194.3 |
| 4 | 235.9 | 217.5 |

What is claimed:

1. A method for performing a non-competitive heterogeneous immunoassay comprising an analyte specific component, an insulating layer, and a fluorescently labelled analyte specific component comprising the steps of
    (a) immobilizing said analyte specific component 1) directly on a reaction well or 2) on a solid phase attached to a reaction well wherein said analyte specific component is in a single continuous region of said reaction well,
    (b) adding an insulating layer which separates the analyte specific component from the labelled analyte specific component, which labelled analyte specific component can be antibodies or antigens, before drying,
    (c) adding said labelled analyte specific component,
    (d) drying said analyte specific component, said insulating layer, and said labelled analyte specific component in said reaction well,
    followed by the steps of:
    (e) adding a sample containing an unknown amount of analyte to be analyzed,
    (f) allowing said analyte to react with said analyte specific component and said labelled analyte specific component,
    (g) washing said well following reaction of said analyte with said analyte specific component and said labelled analyte specific component, and
    (h) detecting a signal from said labelled analyte specific component;
        wherein all reagents other than said sample containing said analyte are added prior to step (e) and wherein said signal is a measure of said unknown amount of analyte in said sample.

2. A method for performing a non-competitive heterogeneous immunoassay comprising an analyte specific component, an insulating layer, and a fluorescently labelled analyte specific component comprising the steps of
    (a) adding a sample containing an unknown amount of analyte to be analyzed to a device comprising: (1) a reaction well; (2) an analyte specific component immobilized directly on a reaction well or on a solid phase attached to said reaction well wherein said analyte specific component is in a single continuous region of said reaction well; (3) a labelled analyte specific component; and (4) an insulating layer which separates the analyte specific component from the labelled analyte specific component, wherein said analyte specific component immobilized on a solid phase, said labelled analyte specific component and said insulating layer have been dried in said well,
    (b) allowing said analyte to react with said analyte specific component and said labelled analyte specific component,
    (c) washing said well following reaction of said analyte with said analyte specific component and said labelled analyte specific component, and
    (d) detecting a signal from said labelled analyte specific component,
        wherein all reagents necessary to perform said non-competitive immunoassay are immobilized or dried on said device prior to adding said sample and wherein said signal is a measure of said unknown amount of analyte in said sample.

3. The method according to claim 1 wherein the reaction well is of the size of an ordinary microtitration well or is smaller than the size of an ordinary microtitration well.

4. The method according to claim 1 wherein step f is carried out in one incubation procedure.

5. The method according to claim 1 wherein said insulating layer comprises protein and/or carbohydrates.

6. The method according to claim 1 wherein said drying is accomplished by air drying.

7. The method according to claim 1 wherein the sample is selected from the group consisting of serum, plasma or whole blood.

8. The method according to claim 1 wherein said labelled analyte specific components comprise lanthanide chelates.

9. The method according to claim 8 wherein the lanthanide chelates are measured by time-resolved fluorometry.

10. The method according to claim 8 wherein the lanthanide chelates are measured either
    a) in solution, or
    b) directly on the solid phase
        by time-resolved fluorometry.

11. The method according to claim 8 wherein two or more different analytes are being measured in one single reaction well by using different lanthanide chelate labels for said two or more different analytes.

12. The method according to claim 1 wherein the analyte is selected from the group consisting of
    a) myoglobin,
    b) creatine kinase isoenzyme MB,
    c) cardiac specific troponin I,
    d) human glycogen phosphorylase isoenzyme BB,
    e) myoglobin and creatine kinase isoenzyme MB, and
    f) myoglobin, creatine kinase isoenzyme MB and cardiac specific troponin I.

13. A device for use in a non-competitive immunoassay comprising
    a) a reaction well,
    b) an analyte specific component immobilized on the surface of the reaction well, either directly or via secondary immobilizing reagents, wherein said analyte specific component is immobilized such that it will not wash off from said reaction well and wherein said analyte specific component is in a single continuous region of said reaction well,
    c) a fluorescently labelled analyte specific component, and
    d) an insulating layer that separates the analyte specific component from the labelled analyte specific component, in which device the analyte specific component, the labelled analyte specific component and the insulating layer all have been dried.

14. The method according to claim 2 wherein the reaction well is of the size of an ordinary microtitration well or is smaller than the size of an ordinary microtitration well.

15. The method according to claim 2 wherein step b is carried out in one incubation procedure.

16. The method according to claim 2 wherein the insulating layer comprises protein and/or carbohydrates.

17. The method according to claim 2 wherein said drying is accomplished by air drying.

18. The method according to claim 2 wherein the sample is selected from the group consisting of serum, plasma or whole blood.

19. The method according to claim 2 wherein said labelled analyte specific components comprise lanthanide chelates.

20. The method according to claim 19 wherein the lanthanide chelates are measured by time-resolved fluorometry.

21. The method according to claim 19 wherein the lanthanide chelates are measured either a) in solution, or b) directly on the solid phase by time-resolved fluorometry.

22. The method according to claim 19 wherein two or more different analytes are being measured in one single reaction well by using different lanthanide chelate labels for said two or more different analytes.

23. The method according to claim 2 wherein the analyte is selected from the group consisting of a) myoglobin, b) creatine kinase isoenzyme MB, c) cardiac specific troponin I, d) human glycogen phosphorylase isoenzyme BB, e) myoglobin and creatine kinase isoenzyme MB, and f) myoglobin, creatine kinase isoenzyme MB and cardiac specific troponin I.

24. A method for performing a competitive heterogeneous immunoassay comprising an analyte specific component, an insulating layer, and a fluorescently labelled analyte or fluorescently labelled analyte analog component comprising the steps of (a) immobilizing said analyte specific component 1) directly on a reaction well or 2) on a solid phase attached to a reaction well wherein said analyte specific component is in a single continuous region of said reaction well, (b) adding an insulating layer which separates the analyte specific component from the labelled analyte or labelled analyte analog component, which labelled analyte or labelled analyte analog component can be antibodies or antigens, before drying, (c) adding said labelled analyte or labelled analyte analog component, (d) drying said analyte specific component, said insulating layer, and said labelled analyte or labelled analyte analog component in said reaction well, followed by the steps of:

(e) adding a sample containing an unknown amount of analyte to be analyzed, (f) allowing said analyte and said labelled analyte or said labelled analyte analog to react with said analyte specific component, (g) washing said well following reaction of said analyte and said labelled analyte or said labelled analyte analog with said analyte specific component, and (h) detecting a signal from said labelled analyte or said labelled analyte analog component;

wherein all reagents other than said sample containing said analyte are added prior to step (e) and wherein said signal is a measure of said unknown amount of analyte in said sample.

25. A method for performing a competitive heterogeneous immunoassay comprising an analyte specific component, an insulating layer, and a fluorescently labelled analyte or fluorescently labelled analyte analog component comprising the steps of (a) adding a sample containing an unknown amount of analyte to be analyzed to a device comprising: (1) a reaction well; (2) an analyte specific component immobilized directly on a reaction well or on a solid phase attached to said reaction well wherein said analyte specific component is in a single continuous region of said reaction well; (3) a labelled analyte or labelled analyte analog component; and (4) an insulating layer which separates the analyte specific component from the labelled analyte or labelled analyte analog component, wherein said analyte specific component immobilized on a solid phase, said labelled analyte or labelled analyte analog component and said insulating layer have been dried in said well, (b) allowing said analyte and said labelled analyte or labelled analyte analog to react with said analyte specific component, (c) washing said well following reaction of said analyte and said labelled analyte or labelled analyte analog with said analyte specific component, and (d) detecting a signal from said labelled analyte or labelled analyte analog component, wherein all reagents necessary to perform said competitive immunoassay are immobilized or dried on said device prior to adding said sample and wherein said signal is a measure of said unknown amount of analyte in said sample.

26. The method according to claim 24 wherein the reaction well is of the size of an ordinary microtitration well or is smaller than the size of an ordinary microtitration well.

27. The method according to claim 24 wherein step f is carried out in one incubation procedure.

28. The method according to claim 24 wherein said insulating layer comprises protein and/or carbohydrates.

29. The method according to claim 24 wherein said drying is accomplished by air drying.

30. The method according to claim 24 wherein the sample is selected from the group consisting of serum, plasma or whole blood.

31. The method according to claim 24 wherein said labelled analyte specific components comprise lanthanide chelates.

32. The method according to claim 31 wherein the lanthanide chelates are measured by time-resolved fluorometry.

33. The method according to claim 31 wherein the lanthanide chelates are measured either a) in solution, or b) directly on the solid phase by time-resolved fluorometry.

34. The method according to claim 31 wherein two or more different analytes are being measured in one single reaction well by using different lanthanide chelate labels for said two or more different analytes.

35. The method according to claim 24 wherein the analyte is selected from the group consisting of a) myoglobin, b) creatine kinase isoenzyme MB, c) cardiac specific troponin I, d) human glycogen phosphorylase isoenzyme BB, e) myoglobin and creatine kinase isoenzyme MB, and f) myoglobin, creatine kinase isoenzyme MB and cardiac specific troponin I.

36. A device for use in a competitive immunoassay comprising
  a) a reaction well,
  b) an analyte specific component immobilized on the surface of the reaction well, either directly or via secondary immobilizing reagents, wherein said analyte specific component is immobilized such that it will not wash off from said reaction well and wherein said analyte specific component is in a single continuous region of said reaction well,
  c) a fluorescently labelled analyte or fluorescently labelled analyte analog component, and
  d) an insulating layer that separates the analyte specific component from the labelled analyte or labelled analyte analog component, in which device the analyte specific component, the labelled analyte or labelled analyte analog component and the insulating layer all have been dried.

37. The method according to claim 25 wherein the reaction well is of the size of an ordinary microtitration well or is smaller than the size of an ordinary microtitration well.

38. The method according to claim 25 wherein step b is carried out in one incubation procedure.

39. The method according to claim 25 wherein the insulating layer comprises protein and/or carbohydrates.

40. The method according to claim 25 wherein said drying is accomplished by air drying.

41. The method according to claim 25 wherein the sample is selected from the group consisting of serum, plasma or whole blood.

42. The method according to claim 25 wherein said labelled analyte specific components comprise lanthanide chelates.

43. The method according to claim 42 wherein the lanthanide chelates are measured by time-resolved fluorometry.

44. The method according to claim 42 wherein the lanthanide chelates are measured either
  a) in solution, or
  b) directly on the solid phase
by time-resolved fluorometry.

45. The method according to claim 42 wherein two or more different analytes are being measured in one single reaction well by using different lanthanide chelate labels for said two or more different analytes.

46. The method according to claim 25 wherein the analyte is selected from the group consisting of
  a) myoglobin,
  b) creatine kinase isoenzyme MB,
  c) cardiac specific troponin I,
  d) human glycogen phosphorylase isoenzyme BB,
  e) myoglobin and creatine kinase isoenzyme MB, and
  f) myoglobin, creatine kinase isoenzyme MB and cardiac specific troponin I.

47. The method according to claim 24 wherein the sample is whole blood.

48. The method according to claim 25 wherein the sample is whole blood.

49. The method according to claim 1 wherein the sample is whole blood.

50. The method according to claim 2 wherein the sample is whole blood.

* * * * *